US011617515B2

(12) United States Patent
Gu et al.

(10) Patent No.: US 11,617,515 B2
(45) Date of Patent: Apr. 4, 2023

(54) MEASUREMENT OF CARDIAC FIRST PHASE EJECTION FRACTION

(71) Applicants: Haotian Gu, Orpington (GB); Philip Jan Chowienczyk, London (GB)

(72) Inventors: Haotian Gu, Orpington (GB); Philip Jan Chowienczyk, London (GB)

(*) Notice: Subject to any disclaimer, the term of this patent is extended or adjusted under 35 U.S.C. 154(b) by 443 days.

(21) Appl. No.: 16/079,645

(22) PCT Filed: Feb. 6, 2017

(86) PCT No.: PCT/GB2017/050290
§ 371 (c)(1),
(2) Date: Aug. 24, 2018

(87) PCT Pub. No.: WO2017/144851
PCT Pub. Date: Aug. 31, 2017

(65) Prior Publication Data
US 2019/0053717 A1 Feb. 21, 2019

(30) Foreign Application Priority Data

Feb. 24, 2016 (GB) .................................. 1603216

(51) Int. Cl.
A61B 5/029 (2006.01)
A61B 5/055 (2006.01)
(Continued)

(52) U.S. Cl.
CPC .............. A61B 5/029 (2013.01); A61B 5/021 (2013.01); A61B 5/026 (2013.01); A61B 5/0245 (2013.01);
(Continued)

(58) Field of Classification Search
CPC ......... A61B 5/029; A61B 5/026; A61B 5/021; A61B 8/065; A61B 8/488
See application file for complete search history.

(56) References Cited

U.S. PATENT DOCUMENTS 5,199,438 A      4/1993   Pearlman
5,846,200 A  *  12/1998   Schwartz ................. A61B 8/08
                                                                600/443
(Continued)

FOREIGN PATENT DOCUMENTS

EP    0846442 A2   6/1998
SU     822812 A1   4/1981

OTHER PUBLICATIONS

Alon Marmor et al: "Radionucide Ventriculography and Central Aorta Pressure Change in Noninvasive Assessment of Myocardial Performance", Journal of nuclear medicine, Oct. 1, 1989 (Oct. 1, 1989), pp. 1657-1665, XP055357405.
(Continued)

Primary Examiner — George R Evanisko
(74) Attorney, Agent, or Firm — Banner & Witcoff, Ltd.

(57) ABSTRACT

Embodiments of the invention provide a method and system for measuring first phase ejection fraction where simultaneous measurement of the systolic pressure during systole of a subject is undertaken at the same time as measurement of the left ventricle volume (LVV). The pressure waveform is then analyzed, for example using automated signal processing techniques, to find a time T1 which corresponds to the point at which the rate of change of systolic pressure during systole begins to reduce. The left ventricle volume at this time T1 is then found from the previous measurements of LVV obtained at the same time as the systolic pressure measurement, and the first phase ejection fraction then calculated in dependence on the LVV at time T1 and the LVV at the start of systole i.e. the end diastolic volume (EDV). In particular embodiments, the first phase ejection fraction is the difference between LVV at EDV and LVV at time T1.

15 Claims, 10 Drawing Sheets

(51) Int. Cl.
      *A61B 8/06*      (2006.01)
      *A61B 8/08*      (2006.01)
      *A61B 5/026*     (2006.01)
      *A61B 5/021*     (2006.01)
      *A61B 5/0245*    (2006.01)

(52) U.S. Cl.
      CPC .............. *A61B 5/055* (2013.01); *A61B 8/065* (2013.01); *A61B 8/0883* (2013.01); *A61B 8/488* (2013.01)

(56) References Cited

U.S. PATENT DOCUMENTS

| | | |
|---|---|---|
| 2003/0004421 A1 | 1/2003 | Ting et al. |
| 2007/0167809 A1 | 7/2007 | Dala-Krishna |
| 2008/0009733 A1 | 1/2008 | Saksena |

OTHER PUBLICATIONS

Robert Slutsky et al, "Comparison of Early Systolic and Holosystolic Ejection Phase Indexes by Contrast Ventriculography in Patients with Coronary Artery Disease", Circulation, Jun. 1, 9180 (Jun. 1, 1980), pp. 1083-1090, XP55357937.
Paul D. Stein, et al, "Rate of change of ventricular power: An indicator of ventricular performance during ejection", American Heart Journal, vol. 91, No. 2. Feb. 1, 1976 (Feb. 1, 1976), pp. 219-227, XP055357512.
Apr. 3, 2017—International Search Report and Written Opinion of International Patent Application No. PCT/GB2017/050290.
Sep. 26, 2016—Search Report of GB Application No. 1603216.1.
Circulation, 66, Sep. 1982, Dallas, Texas (USA), Chen et al., "Left Ventricular Myocardial Blood Flow in Multi-vessel Coronary Artery Disease", pp. 537-547.
Sep. 30, 2019—(EP) Office Action—App 17 704 070.6.
Söderqvist Emil et al., "Feasibility of Creating Estimates of Left Ventricular Flow-Volume Dynamics Using Echocardiography," Cardiovascular Ultrasound, Biomed Central, London, GB, vol. 4, No. 1, Oct. 31, 2016, 11 pages.

* cited by examiner (a)

(b)

(a)

(b)

MEASUREMENT OF CARDIAC FIRST PHASE EJECTION FRACTION

CROSS-REFERENCE TO RELATED APPLICATIONS

This application is a U.S. National Stage application under 35 U.S.C. § 371 of International Application PCT/GB2017/050290 (published as WO 2017/144851 A1), filed Feb. 6, 2017, which claims the benefit of priority to Application GB 1603216.1, filed Feb. 24, 2017. Benefit of the filing date of each of these prior applications is hereby claimed. Each of these prior applications is hereby incorporated by reference in its entirety

TECHNICAL FIELD

Embodiments of the present invention relate to a method and system for measurement of the ejection fraction from the left ventricle of the heart during the onset of systole. The value of the measured ejection fraction has been found to be indicative of a higher possibility of the development of heart disease and gives an early indicator thereof.

BACKGROUND TO THE INVENTION AND PRIOR ART

Early identification of heart problems and heart disease allows for more effective treatment, and preventative action to be undertaken to slow or stop the disease progression. As one of the most common health issues, any improvement in identification of early-onset symptoms of heart disease is highly desirable.

SUMMARY OF THE INVENTION

Shortening-deactivation of cardiac myocytes provides a mechanism linking systolic to diastolic dysfunction whereby an impairment of early systolic ejection leads to sustained myocardial contraction, preserving overall ejection fraction at the expense of diastolic dysfunction. To try and detect such impairments, an index of first-phase ejection fraction (EF1), being the fraction of left ventricular volume ejected from the start of systole to the time of the first peak in LV pressure (corresponding to the time of maximal ventricular shortening), was formulated to examine the relationship of early phase ejection to duration of myocyte contraction and diastolic relaxation in patients with hypertension (n=163) with varying degrees of diastolic dysfunction but in whom overall ejection fraction was preserved. LV systolic pressure was estimated by carotid tonometry; time-resolved LV cavity and wall volume were obtained by echocardiography with speckle wall-tracking. Measurements were repeated after nitroglycerin, a drug known to influence ventricular dynamics, in a sub-sample (n=18) of patients. EF1 and time of onset of ventricular relaxation (TOR, as determined from the temporal pattern of myocardial wall stress) were strongly correlated (standardized regression coefficients −0.36 and 0.35 respectively, each P<0.0001) with diastolic relaxation (transmitral:tissue Doppler E/E' ratio) irrespective of adjustment for age, sex, anti-hypertensive treatment, measures of afterload and ventricular geometry. Nitroglycerine increased EF1, decreased TOR and improved diastolic relaxation. The conclusions reached include that hypertensive patients with diastolic dysfunction exhibit reduced first-phase ejection fraction and sustained myocardial wall stress. Impaired shortening may sustain myocardial contraction preserving systolic ejection fraction at the expense of impaired relaxation. As a consequence, a technique for the measurement of first phase ejection fraction will help in the early identification and diagnosis of patients with such dysfunction earlier that heretofore has been the case.

Embodiments of the invention therefore provide a method and system for measuring first phase ejection fraction where simultaneous measurement of the systolic pressure during systole of a subject is undertaken at the same time as measurement of the left ventricle volume (LVV). The pressure waveform is then analyzed, for example using automated signal processing techniques, to find a time T1 which corresponds to the point at which the rate of change of systolic pressure during systole begins to reduce. The left ventricle volume at this time T1 is then found from the previous measurements of LVV obtained at the same time as the systolic pressure measurement, and the first phase ejection fraction then calculated in dependence on the LVV at time T1 and the LVV at the start of systole i.e. the end diastolic volume (EDV). In particular embodiments, the first phase ejection fraction is the difference between LVV at EDV and LVV at time T1.

In view of the above, from a first aspect there is provided a method, comprising: i) monitoring the left ventricle volume of a test subject during at least a first part of a cardiac cycle; ii) determining a point in time in the cardiac cycle which is the end of a first phase of ventricular contraction during the first part of the cardiac cycle; and iii) calculating a first phase ejection measurement in dependence on the left ventricle volume at the start of the first part of the cardiac cycle and the left ventricle volume at the determined point in time in the cardiac cycle which is the end of the first phase of ventricular contraction.

In one embodiment the point in time in the cardiac cycle which is the end of the first phase of ventricular contraction is the point in time at which the rate of change of the systolic pressure during the first part of the cardiac cycle reduces. Alternatively, in another embodiment the point in time in the cardiac cycle which is the end of the first phase of ventricular contraction is the point in time that corresponds to the time of a first peak in systolic pressure.

Moreover, in a further embodiment the point in time in the cardiac cycle which is the end of the first phase of ventricular contraction is the point in time that corresponds to the time of maximal rate of ventricular shortening. In some embodiments this can be measured as the peak motion of myocardial tissue, for example measured using tissue Doppler imaging.

Additionally, in a yet further embodiment the point in time in the cardiac cycle which is the end of the first phase of ventricular contraction is the point in time that corresponds to a first shoulder on the systolic pressure waveform;

Furthermore, in another embodiment the point in time in the cardiac cycle which is the end of the first phase of ventricular contraction is the point in time that corresponds to peak aortic flow or peak aortic flow velocity.

All of the above variations on the defined point in time for T1 give physiologically meaningful measurements personalised to the particular patient subject (rather than, for example, simply defining a point in time after the onset of systole to perform measurements based on some statistical measurement from prior studied groups of patient subjects), and hence more meaningful and accurate diagnostic prediction of heart disease onset specific to the individual patient subject can be obtained.

Further features and advantages will be apparent from the appended claims.

BRIEF DESCRIPTION OF THE DRAWINGS

Embodiments of the invention will now be described with reference to the accompanying drawings, wherein like reference numerals refer to like parts, and wherein:—

OVERVIEW OF EMBODIMENTS

Heart failure (HF) was thought to result from the reduction of left ventricular (LV) systolic function. Ejection fraction (EF), a measure of percentage of blood volume ejected during systole, has been used widely as a gold standard of assessing systolic function and quantify degree of HF.

EF can be calculated from the following equation:

$$EF=(EDV-ESV)/EDV \qquad (Eq.\ 1)$$

where EDV=end-diastolic LV volume, ESV=end-systolic volume.

It has become widely recognized that HF can occur when EF is preserved, especially in the early stage, and diagnosis can be difficult.

Ventricular contraction is a time-varying phenomenon and is determined by various parameters such as myocytes shortening and arterial load. As a consequence, EF as a measurement between two single points defining the start and end of systole may not adequately reflect this complex phenomena. Instead, we have found that it is necessary to make measurements of ejection fraction during different parts of the systole phase of the cardiac cycle, and that such measurements can be indicative of early onset heart failure.

In particular, we have found that an intra-systolic phase measurement of ejection fraction that measures ejection fraction over only part of the systole phase, rather than ejection fraction over the whole systole phase, is meaningful in that we have found it to be a good indicator of possible early onset heart failure. In particular, the preferred intra-systolic phase ejection fraction measurement that we have found to be of most use is a measurement that we refer to herein as the 1st phase ejection fraction (EF1), being a time-varying phenomenon of volume change of the left ventricle during the initial phase of LV contraction. In particular, EF1 measures the percentage of LV volume change from end-diastole (ED) to the end of initial ventricular contraction at a time we then define as T1. This time T1 defining the end of initial ventricular contraction in some instances corresponds to the time of the first peak in ventricular systolic pressure, and approximates the time of maximal rate of ventricular shortening. In other instances it corresponds to the first shoulder on the measured pressure waveform; that is, the first point where the rate of change of pressure with respect to time itself changes. More generally, it corresponds to the first point in time in the systolic pressure waveform where the rate of change of pressure reduces, whether this is at a peak in the systolic pressure waveform, or at a shoulder in a still increasing systolic pressure waveform.

Figure 7:
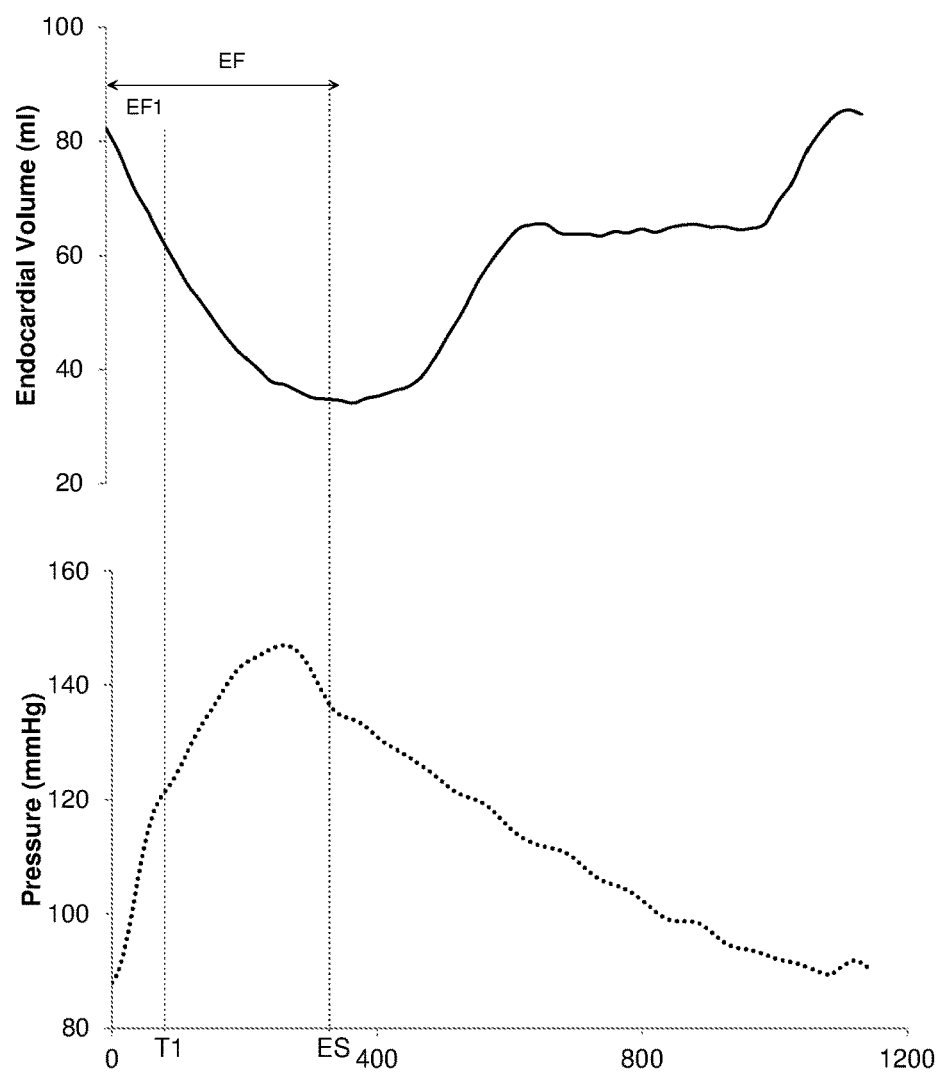
FIG. 7 is a pair of charts showing left ventricular volume curve (upper figure) and pressure waveform (lower figure). EF1 is defined as the volume change from the initial point to T1; EF is defined the volume change from initial point to end-systole (ES). In order to determine T1, central aortic pressure waveform derived by carotid tomometry is used. T1 is defined as the first shoulder on the pressure waveform in this example.

Once the point T1 has been identified in the systolic pressure waveform, the first phase ejection fraction EF1 can then be calculated from the following equation:

$$EF1=(EDV-T1V)/EDV\ \% \qquad (Eq.\ 2)$$

where EDV=end-diastolic LV volume, T1V=volume at T1 (see FIG. 7).

Figure 6:
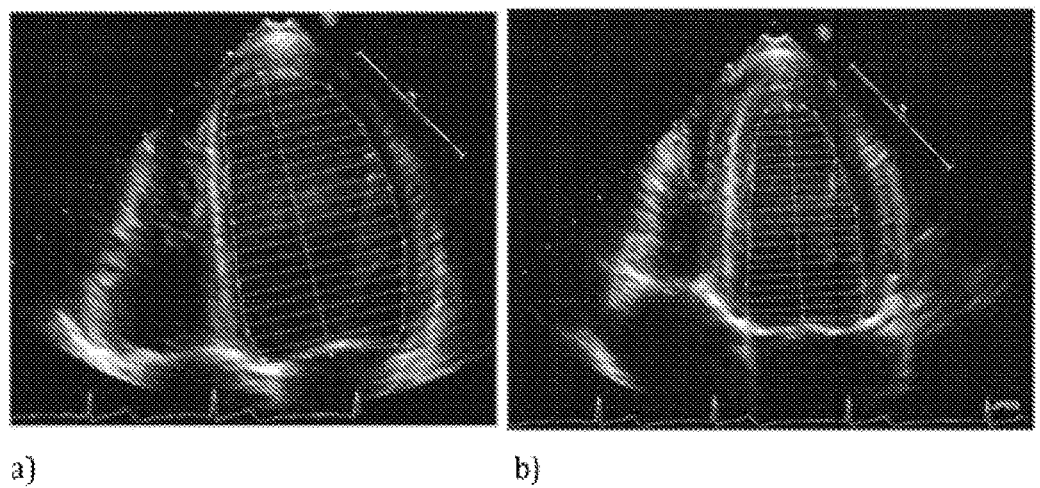
FIG. 6 is a pair of Echo images showing: a) Left ventricular volume at end-diastole (largest cavity size); and b) Left ventricular volume at end-systole (smallest cavity size).
Figure 8:
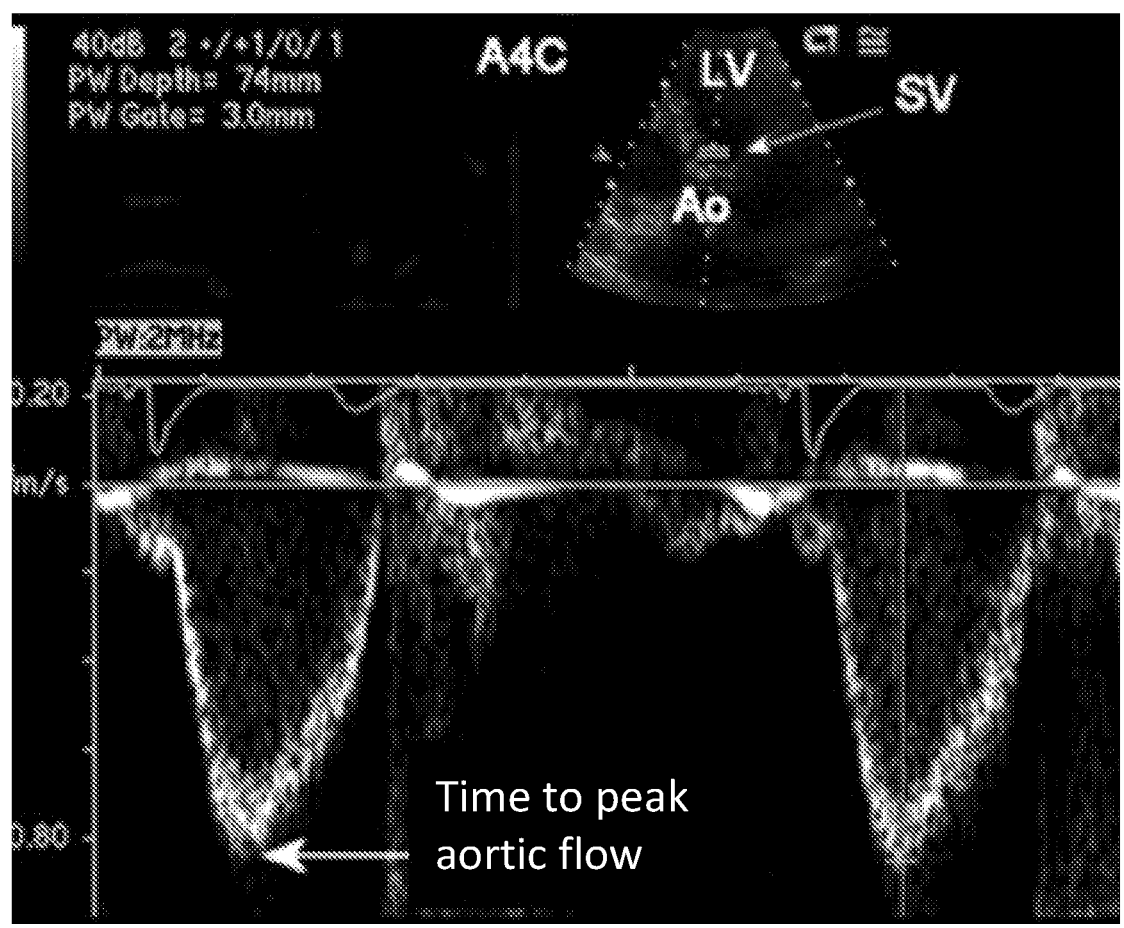
FIG. 8 is a Pulse wave Doppler image that shows that the time to peak aortic flow can be derived from Echocardiographic Doppler imaging.

With regards to obtaining the LV volume data, time-varying LV volume waveforms can be derived from contemporary echocardiographic speckle tracking techniques (see for example FIGS. 6(a) and (b), which shows examples of how the LV can be tracked in such images and the volume determined therefrom) or Cardiac Magnetic Resonance Imaging (CMRI). The time of initial ventricular contraction can be determined by non-invasive central pressure measurements (see FIG. 7, bottom chart, which shows an example pressure waveform), for example using carotid tonometry techniques known already in the art, or measuring time to peak aortic flow using, for example, Echocardiographic Doppler techniques, as also already known in the art. FIG. 8 gives an example Doppler image showing such a measurement.

Figure 9:
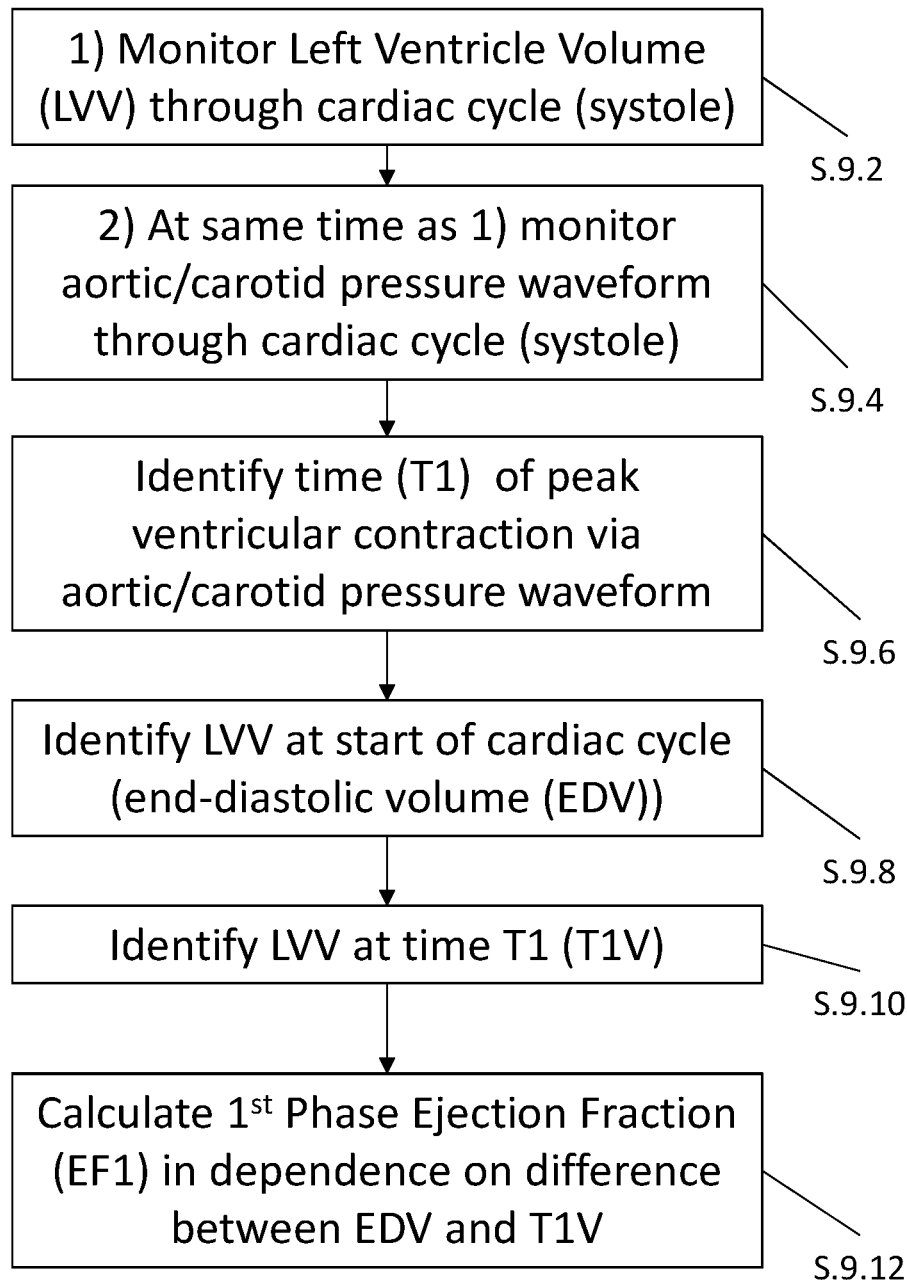
FIG. 9 is a flow diagram illustrating the steps performed in an embodiment of the invention.

In view of the above, FIG. 9 is a flow diagram showing the steps involved in an embodiment of the invention. Firstly, at s.9.2 and 9.4, which are conducted at the same time, on a test subject monitor the left ventricle volume through the whole cardiac cycle, or at least through the systole phase, and record the monitored volumes. As noted above, this monitoring of the LVV may be accomplished via echo speckle tracking techniques, or CMRI techniques, both of which are known already in the art. In addition to monitoring the LVV of the subject, at the same time the aortic or carotid pressure waveform of the test subject is also monitored throughout the cardiac cycle, or at least through the systole phase, for example using carotid tonometry or Echo Doppler techniques. Thus after s.9.4 time aligned data representing both the LVV and the aortic or carotid pressure waveform in the test subject have been obtained. Once these simultaneous steps have been performed and the time aligned data obtained, the presence of the test subject is no longer required. The remaining steps may therefore be performed later, separately from the test subject without the subject being present.

Therefore, having obtained the time aligned data from the test subject, that time-aligned data may then be analyzed to determine the desired measurement of first phase ejection fraction. Therefore, the next step, at s. 9.6, is to analyze the aortic or carotid pressure waveform to identify the time T1 from the aortic or carotid pressure waveform. As discussed above, the time T1 corresponds to the first point in time in the systolic pressure waveform where the rate of change of pressure reduces, whether this is at a peak in the systolic pressure waveform, or at a shoulder in a still increasing systolic pressure waveform. One way of finding this point T1 in the pressure waveform systematically (and hence capable of being implemented automatically) is to undertake suitable signal processing on the waveform to detect the point, given the characteristics above. One example of the signal processing that may be undertaken is to differentiate the aortic or carotid pressure waveform with respect to time to identify the first point in time during systole where the rate of change of aortic or carotid pressure reduces, and define T1 as this identified point. If necessary, in some embodiments second order differentiation of the pressure waveform will make identification of the point T1 even easier, as a hump or spike in the second order differential waveform will be present at the point in the pressure waveform where the rate of change first changes.

Having identified the point in time T1 of peak ventricular contraction via the change in the rate of change in the aortic or carotid pressure waveform, at s.9.8 the LVV at the start of systole (also known as the end-diastolic volume (EDV)) is found, from the LVV data recorded at s.9.2. Then, at s. 9.10, the time-aligned LVV data is then referenced, using the identified T1 time as a time index into the LVV data to identify the LVV at time T1. Having obtained the EDV from s.9.8, and the LVV at T1, the first phase ejection fraction EF1 is then found in dependence on the difference between the EDV and the LVV at time T1 i.e the T1V. Specifically, in some embodiments EF1 is found using the equation (2) set out above.

Figure 10:
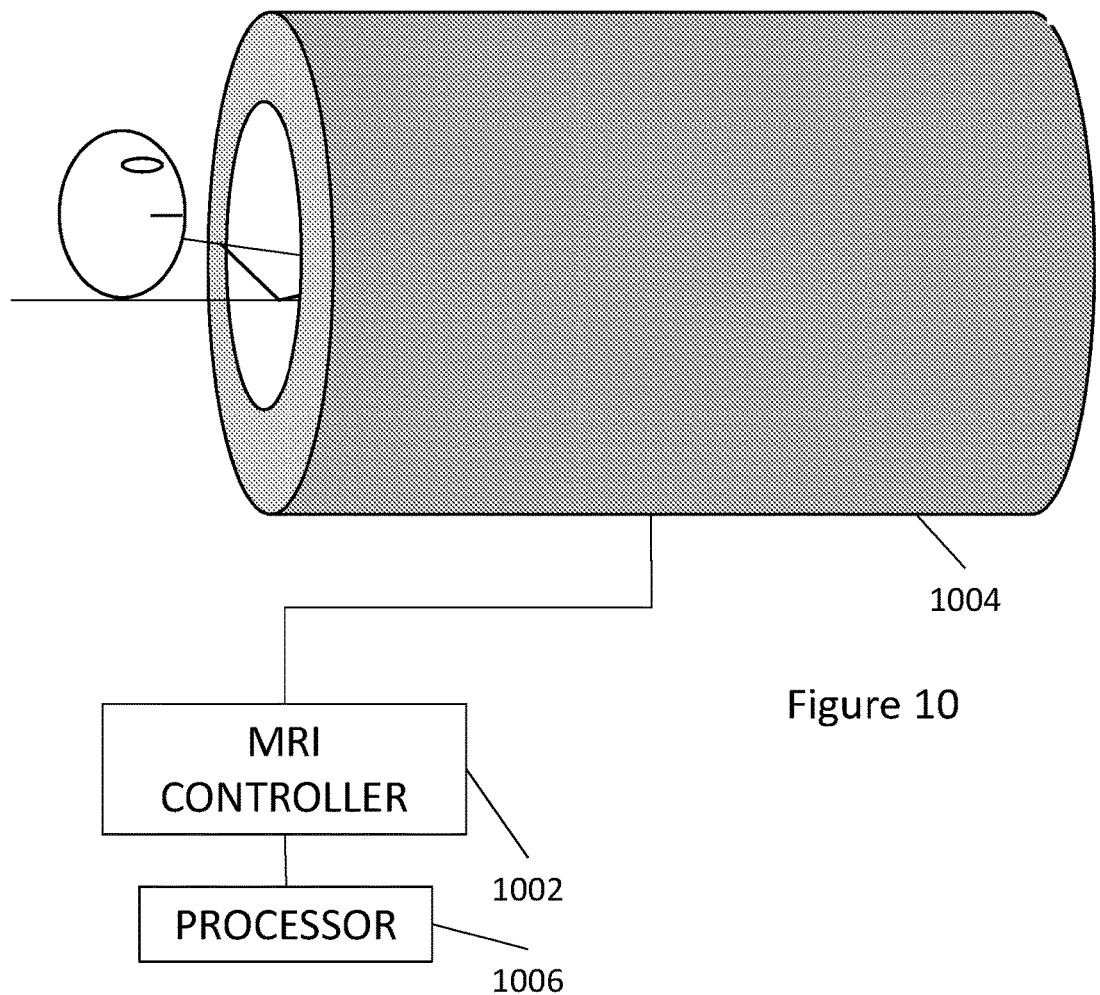
FIG. 10 is a simplified diagram of an MRI scanner that may be used as the basis for an embodiment of the invention.

Regarding medical imaging systems that may perform the above method in further embodiments of the invention, as mentioned previously, echocardiographic speckle tracking systems or cardiac MRI systems may undertake the LVV monitoring, whilst carotid tonometry or echocardiographic Doppler systems undertake the simultaneous aortic pressure wave monitoring. FIG. 10 shows a CMRI system 1004 having an MRI controller 1002 for controlling the operation of the CMRI system and a processor 1006. The processor 1006 in use can receive the LVV data from the CMRI system and aortic or carotid pressure waveform data (for example from a carotid tonometry system (not shown)) and then find the first phase ejection fraction using the method of FIG. 9.

Figure 11:
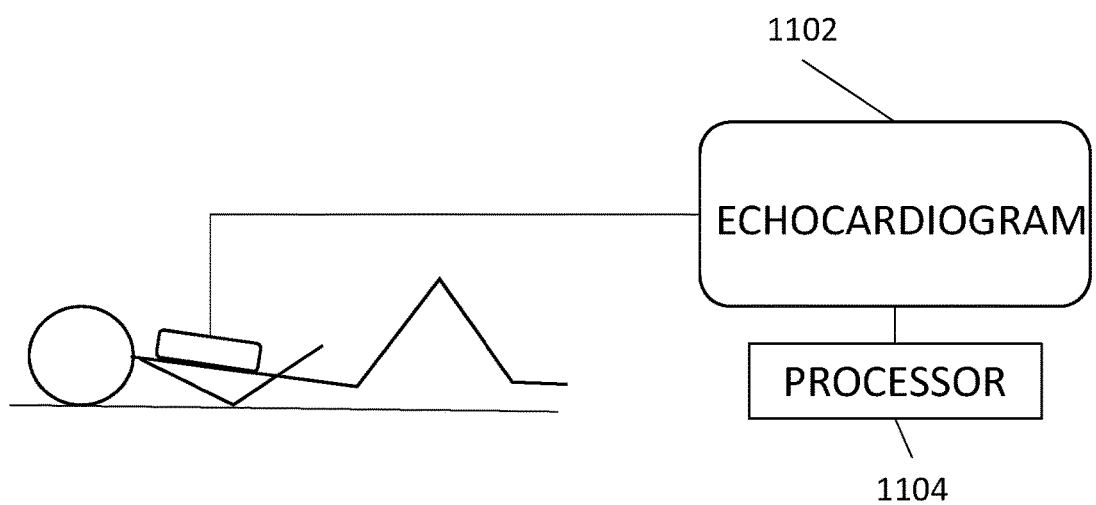
FIG. 11 is a simplified diagram of an ECG monitor that may be used as the basis for an embodiment of the invention.

Similarly, where echocardiography is use instead of MRI techniques, FIG. 11 show an echo system 1102, having a processor 1104. Again, here the processor 1104 in use can receive the LVV data from the echo system and aortic or carotid pressure waveform data from a carotid tonometry system (not shown) and then find the first phase ejection fraction using the method of FIG. 9.

Figure 12:
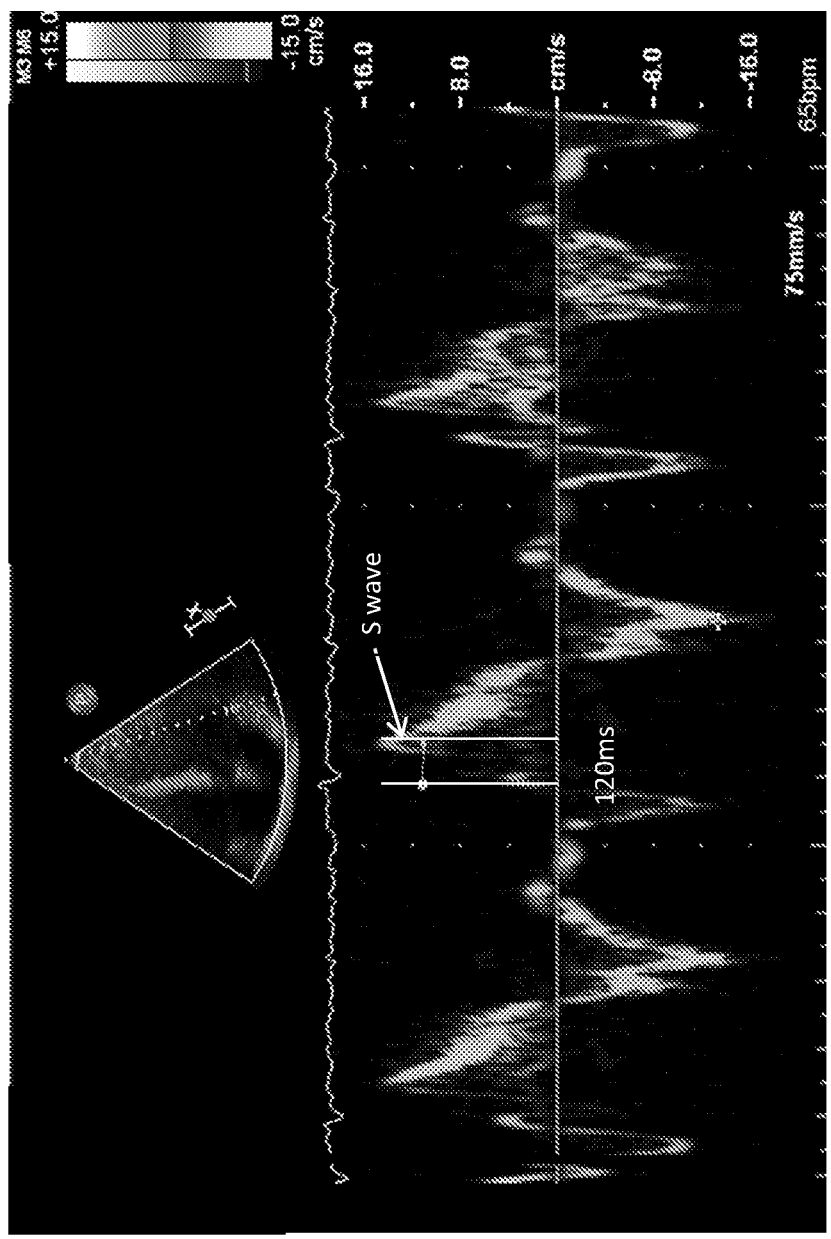
FIG. 12 is a tissue doppler image showing the point of peak motion of myocardial tissue.

An alternative imaging technology to identify the point T1 is to use tissue Doppler imaging (TDI) to identify the peak motion of the myocardial tissue. FIG. 12 illustrates such a TD trace, where the tissue Doppler imaging S wave reflects the peak motion of the myocardial tissue during systole. The time to point T1 can also be defined using TDI, as the time between the R wave on an ECG to the peak of the S wave, as shown in FIG. 11. Using TDI in this manner to determine the peak motion of myocardial tissue is one way of determining of the maximal rate of ventricular shortening i.e. the point at which the heart tissue is contracting the fastest. Having determined T1 using this technique, the LVV volume change can then be measured during this period using the techniques described above.

To summarize the above, therefore, embodiments of the invention provide a new measurement technique that involves two processes. The first process is to identify the "first-phase" of ejection as the time from the start of systole to a time T1 early in systole. As explained above, one such time T1 may be the time at which the rate of change of volume of the LV (i.e. of myocardial shortening) is maximal. In some embodiments of the invention this can be identified in a number of ways:

a. As the time of the first systolic shoulder of a central aortic or carotid pressure waveform;
  b. As the time of peak aortic flow or flow velocity;
  c. As the time of maximal rate of change of volume of the ventricle;
  d. As an absolute time close to the average time of the above (e.g. 100 msec); or
  e. As a fraction of the ejection duration (e.g 10% of the ejection duration) that corresponds to the above.

Applying one of the above timing criteria gives the time T1 to which the ejection fraction should be measured, for it to be considered the "first-phase" ejection fraction, as discussed herein. Having found this time, the second process that is required by embodiments of the invention is to then measure the volume change from the start of systole to the identified time T1 to thereby give the desired "first-phase" ejection volume (EV1). As described previously and below, this volume measurement may also be performed in a number of ways. For example, the volume change measurement may be performed by any of:

i). Echocardiography using speckle tracking of the movement of the walls of the ventricle;

ii). Magnetic resonance imaging (MRI) to track movement of the walls of the ventricle; and/or iii). Measurement of aortic flow velocity by echocardiography or MRI and integration of aortic flow velocity or aortic flow (derived from velocity and aortic cross-sectional area) from the start of systole to time T1. If measured as an integral of aortic velocity then when expressed as the ratio to total ejection volume a ratio EF1R as defined below will be obtained this obviates the need to measure aortic cross-sectional area.

As noted, EV1 may be expressed as an absolute volume or as a percentage of end-diastolic volume to give a "first-phase" ejection fraction (EF1), or more alternatively as a percentage of overall ejection volume to give EF1 as a fraction of overall ejection fraction (EF1R). Any of these values are suitable outputs conveying essentially the same or similar information i.e. information relating to the amount of blood ejected from the heart during the identified first phase of the cardiac cycle.

With the above arrangements, therefore, a new measurement referred to herein as the first phase ejection fraction is found, being a time-varying phenomenon of volume change of the left ventricle during the initial phase of LV contraction. As mentioned above and discussed further below, the first phase ejection fraction has been found to be a good early indicator of early on-set heart failure. Early identification thereof therefore allows for improved treatment regimes and better clinical outcomes to be obtained.

Detailed Discussion of Embodiments

Further details of embodiments of the invention will now be described, and the results obtained therefrom discussed.

Introduction

Figure 1:
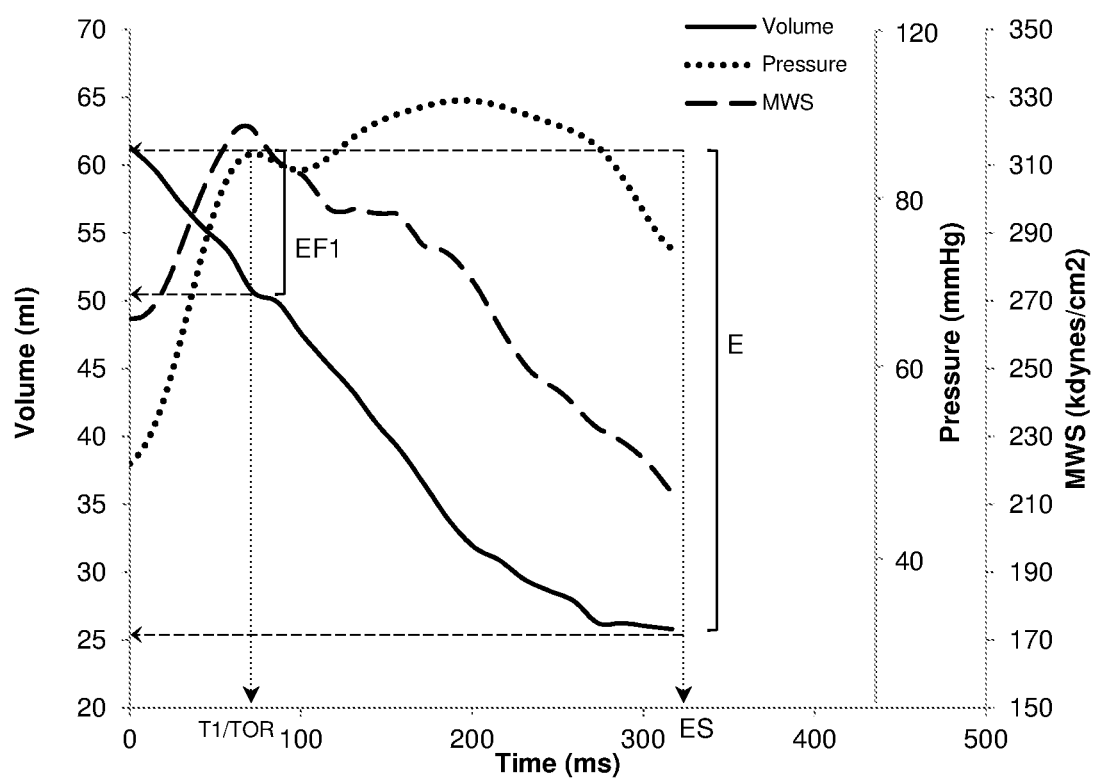
FIG. 1 shows the endocardial volume curve (solid line) obtained by echo wall-tracking, central aortic pressure waveform (dotted line) obtained by carotid tonometry, together with ejection-phase myocardial wall stress (dashed line), computed from the central aortic systolic pressure waveform and instantaneous left ventricular dimensions in a normotensive subject. Myocardial wall stress starts to fall at the first peak of central aortic pressure (T1, coinciding with peak aortic flow and maximal ventricular shortening). EF1 is percentage volume change between end-diastole and T1.

Isolated myocytes, especially cardiac myocytes, exhibit "shortening-deactivation"[1,2] whereby shortening of the myocyte after depolarization leads to a fall in tension compared to that observed under isometric conditions. This mechanism occurring in vivo could contribute to the rapid reduction in myocardial wall stress (which approximates tension per cross-sectional area in individual myocytes) that, in healthy subjects, occurs early in systole at a time close to that of the maximal rate of shortening of the myocardium,[3] and which may facilitate relaxation in diastole (FIG. 1). Conversely an impairment of early-phase ejection would be expected to result in an impairment of deactivation and hence sustain myocardial wall stress to preserve total ejection fraction at the expense of impaired diastolic relaxation.

We examined this possibility by formulating a novel index of early-phase ejection: first-phase ejection fraction (EF1), the ejection fraction up to the time of the first peak in ventricular systolic pressure (T1, approximating the time of maximal rate of ventricular shortening). We examined the relationship between EF1, the time of onset of myocardial relaxation (TOR, as measured from the temporal pattern of myocardial wall stress) and diastolic relaxation (E/E', the ratio of early transmitral flow velocty E to tissue Doppler early mitral annular movment E') in patients with hypertension in whom some degree of diastolic dysfunction is common but in whom ejection fraction and systolic function, as measured by conventional indices, is preserved. In a sub-sample of patients we examined changes in EF1, TOR and E/E' before and after administration of nitroglycerine, a drug that influences ventricular dynamics[4,6] and which is thought to decrease the TOR as do other nitric oxide (NO) donors.[6]

Methods

Study Population

Subjects (n=163; 83 men; mean±SD age 46.5±16.5 years) were recruited from those who were evaluated for hypertension at Guy's and St Thomas' Hospital, London, Hypertension Clinic. Subjects with significant valvular disease, impaired left ventricular systolic function (ejection fraction <45%) and arrhythmia other than sinus arrythmia were excluded. The study was approved by the London Westminster Research Ethics Committee, and written informed consent was obtained. Anthropometric and clinical data were collected on a single study day and included medical and drug history, measurement of height and weight, measurement of peripheral and central blood pressure (BP), aortic root pulse wave velocity (PWV), echocardiography and myocardial wall stress.

Blood Pressure and Aortic Root Pulse Wave Velocity

Peripheral brachial blood pressure (BP) was measured in a seated position using an Omron HEM 705-CP semiautomatic oscillometric recorder. The mean of three values of peripheral systolic BP (SBP) and diastolic BP (DBP) were used for analysis.

Carotid and radial arterial pressure waveforms were obtained by a high-fidelity micromanometer (SPC-301; Millar Instruments, Houston, Tex.) and processed by the SphygmoCor device (Atcor medical, Australia) from the left radial and left carotid artery. Radial waveforms meeting the inbuilt quality control criteria of the SphygmoCor device were averaged and calibrated from peripheral brachial measures of SBP and DBP, from which mean arterial pressure (MAP) was calculated by integrating the radial waveform. The carotid pressure waveform was then calibrated from MAP and peripheral DBP (which unlike SBP are equal at aortic and peripheral sites[7,8]). Previous studies have shown that because of its close proximity to the aorta, the carotid waveform can be used as a surrogate of the central aortic pressure waveform and left ventricular pressure during systole.[9] The carotid waveform thus calibrated was used to identify the time to first systolic shoulder of the central pressure waveform (T1, FIG. 1) which closely approximates the time of maximal aortic flow and ventricular shortening.

Aortic root pulse wave velocity (PWV) was calculated by the single-point technique[10] (the sum of squares method), using the following equation:

$$PWV = \frac{1}{\rho}\sqrt{\frac{\sum dP^2}{\sum dU^2}}$$

where ρ is the density of blood, P is central aortic pressure (derived from carotid pressure by SphygmoCor), U is aortic flow velocity (derived from echocardiography pulse wave Doppler in the aortic root from an apical 5-chamber view).

Echocardiography, Time-Resolved Left Ventricular Dimensions and First-Phase Ejection Fraction A transthoracic echocardiographic study was obtained using the GE Vivid 7 ultrasound system (GE Healthcare, Little Chalfont, UK) and analysed by one author (H.G) whilst blinded to relevant clinical information. All echocardiographic views and measurements were performed using standard techniques according to the American Society of Echocardiography (ASE).[11] Frequency and frame rate were optimized to allow adequate penetration for endocardial and epicardial border definition. Left ventricular (LV) mass (LVM) was measured by two-dimensional M-mode according to ASE recommendations.[11] LVM index (LVMI) was calculated by dividing LVM by body surface area (BSA). Pulsed wave Doppler was performed using a 5 mm sample volume at the tips of mitral leaflets in 4-chamber view with a sweep speed of 150 mm/s. Tissue Doppler measures were obtained at levels of the lateral and septal mitral annulus to obtain an optimal spectral Doppler waveform. The E/E' ratio was then calculated as a measure of diastolic relaxation from the ratio of the transmitral Doppler E wave velocity to the mean tissue Doppler E' wave. Aortic flow velocity was obtained via Pulsed wave Doppler below aortic valve from apical 5-chamber view. Global longitudinal strain (GLS) was calculated using a GE EchoPAC analysis package (GE healthcare, Little Chalfont, UK) from apical 4, 2 and 3 chamber views.

Figure 2:
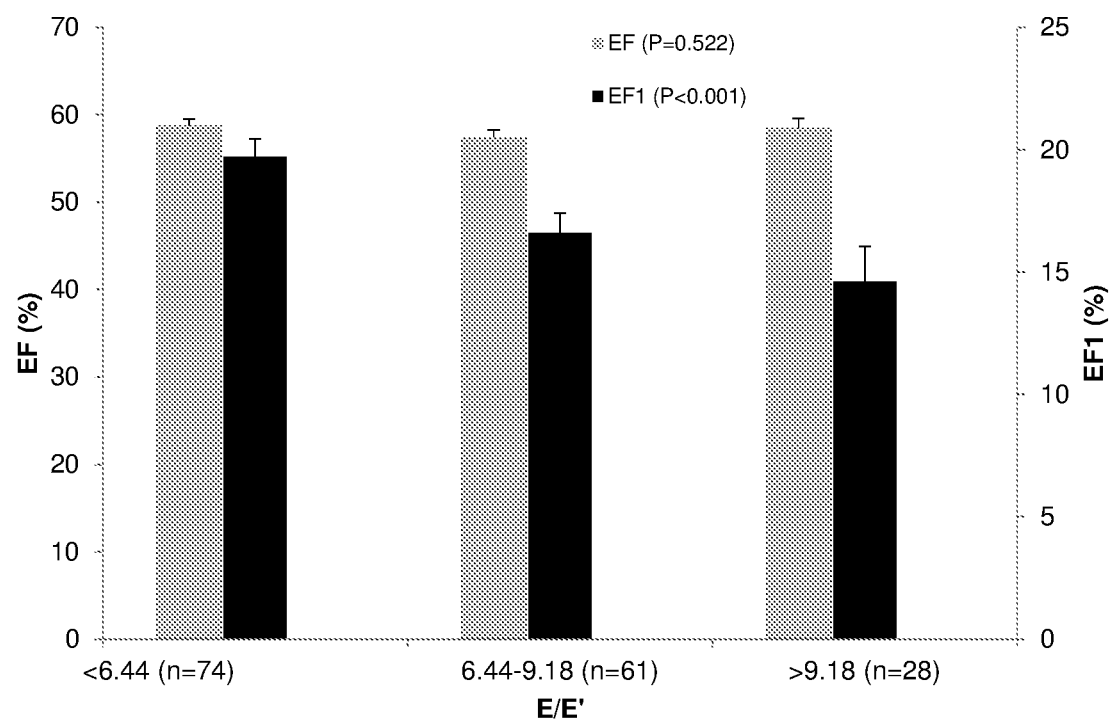
FIG. 2 shows the total systolic ejection fraction (EF, gray bars) and first-phase ejection fraction (EF1 (black bars, see FIG. 1 for explanation) in three groups defined according to E/E'. Total EF was preserved and was similar between groups. EF1 was significant lower in subjects with impaired diastolic relaxation compared to those with preserved diastolic relaxation.

Time-resolved cavity volume and myocardial wall volume were measured using a Tomtec analysis package (2D cardiac performance analysis, Tomtec, Munich, Germany) from a 2D apical 4-Chamber view with optimized gain and depth using both endocardial and epicardial definition. The endocardium was initially defined by placing at least 6 points along it; the width of interest was then adjusted to accommodate myocardial thickness in each frame. Both the endocardial and epicardial border were then tracked automatically throughout the whole cardiac cycle (FIG. 2). Auto-tracking was reviewed and edited frame by frame to ensure accurate tracking. End-diastolic volume (EDV) and End-systolic volume (ESV) were derived from the LV volume curve. Ejection Fraction (EF) was calculated as a percentage change of (EDV-ESV)/EDV.

First-phase ejection fraction (EF1) was introduced as a novel measure of early systolic ventricular function. EF1 is the percentage change in LV volume from end-diastole to T1 on the central aortic waveform (FIG. 1), a time that approximates the time of peak ventricular contraction in individual myocytes. EF1 is thus given by:

$$EF1 = (EDV - T1V)/EDV \%$$

where EDV is end-diastolic endocardial volume and T1V is endocardial volume at T1. Coefficients of variation (CV) defined as the ratio of the SD to mean for measurements of LV cavity and wall volumes obtained from the same image analysed on 2 different occasions were <5%. Times of aortic valve opening (AVO) and closure (AVC) were obtained from aortic valve spectral Doppler. Ejection duration was then defined from the beginning of AVO to AVC.

Time-Varying Myocardial Wall Stress

Myocardial wall stress (MWS) was obtained from the Arts[12] formula:

$$MWS = \frac{P}{\frac{1}{3}\ln\left(1 + \frac{V_w}{V_{lv}}\right)}$$

where P is LV pressure, ln, natural logarithm, $V_w$, myocardial wall volume, $V_{lv}$, LV cavity volume and $V_w$ is the difference between LV epicardial wall volume and $V_{lv}$. Carotid applanation tonometry and echocardiography with wall tracking (as above) were used to obtain LV pressure, and LV wall and cavity volume, respectively, over time during systole and hence to obtain time-resolved systolic MWS from the Arts formula as previously described by Chirinos et al.[3] Time of onset of relaxation (TOR) of MWS was defined as the time from the start of systole to peak MWS and expressed as a percentage of ejection duration.

Systolic and Diastolic Function in Response to Nitroglycerin

Measurements of blood pressure, PWV, ventricular dynamics and wall stress described above were repeated in a sub-sample of 18 subjects (14 men, aged 43.0±11.9 years). Measurements were performed at baseline and then between approximately 5 to 15 min after 400 hg of NTG delivered sublingually (when haemodynamic measurements were approximately stable).

Statistical Analysis

Characteristics are summarized as means±standard deviation (SD) and results as means±standard error of the mean (SEM). To examine the relationship between ventricular ejection and duration of contractility (EF1 and TOR) with E/E' ratio, all subjects were divided into 3 groups according to previously recognized thresholds:[13] group one (E/E'<6.43), group two (E/E' 6.44-9.18), group three (E/E'>9.18). Comparisons between these groups were then made using analysis of variance (ANOVA) with adjustment for confounding factors. Multiple regression analysis was used to examine the relation between EF1 and TOR with E/E', treating E/E' as a continuous variable. The following variables were forced into the multivariate models: age, sex, BMI, anti-hypertensive medications, SBP, DBP, heart rate (HR) and T1, LV EDV, PWV and AV peak flow. In addition, the analysis was repeated using MAP rather than SBP and DBP and using backward stepwise regression. Goodness of fit was expressed as the adjusted $r^2$. Changes from baseline in haemodynamic measures after NTG were compared using Student's paired t-test. A p-value <0.05 was considered statistically significant and all tests were 2-tailed. Statistical analyses were performed using SPSS (SPSS Inc, Chicago, Ill., version 21).

Results

Subject Characteristics

Subject characteristics in groups defined by E/E' are shown in table 1. Subjects with higher E/E' were older than those with lower E/E' and there were proportionally more women in groups with higher compared to lower E/E'. Those with higher E/E' also had higher blood pressure, higher LVMI and were more likely to be taking anti-hypertensive medications. All subjects had preserved left ventricular systolic function (EF>45%). There was no significant difference in heart rate, EF or global longitudinal strain across groups with varying E/E'.

First-Phase Ejection Fraction and Diastolic Relaxation

Whilst overall ejection fraction (and also global longitudinal strain) were similar across groups with increasing E/E', EF1 was lower in subjects with higher E/E' (FIG. 2). In subjects with the highest E/E' (>9.19), EF1 was 14.6±5.6% compared to 19.7±6.2% in the lowest group (E/E'<6.43, p<0.001, irrespective of adjustment for age and gender or other covariates), i.e. a 26% difference in EF1 between these groups. In multivariate regression (with all covariates forced into the model), EF1 was strongly correlated with E/E' (β=−0.359, p<0.001). On stepwise regression it was equally strongly correlated with E/E' and less strongly or weakly correlated with gender, DBP (or MAP when MAP was substituted for SBP and DBP) and use of anti-hypertensive medication (table 2).

Duration of Myocardial Contraction and E/E'

Figure 3:
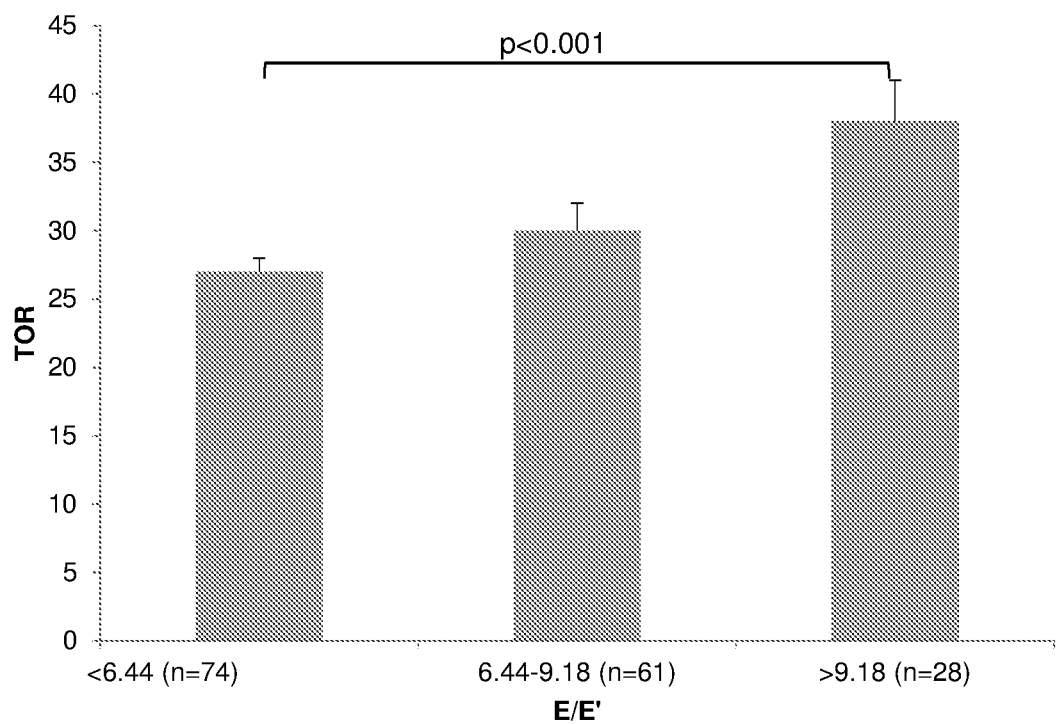
FIG. 3 illustrates the time from end-diastole to onset of myocardial relaxation (TOR) in three groups defined according to E/E'. Myocardial contraction was sustained to a greater extent in subjects with impaired diastolic relaxation compared to those with preserved diastolic relaxation with TOR higher in subjects with impaired relaxation.
Figure 4:
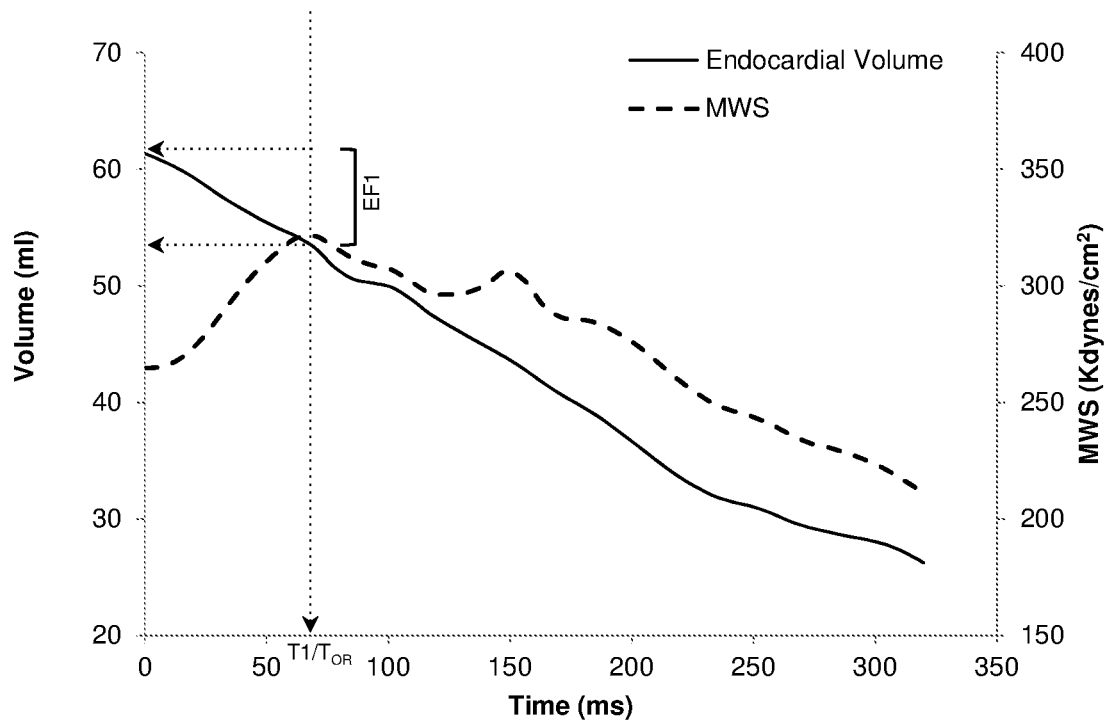
FIG. 4 shows typical endocardial volume and myocardial wall stress traces in patients with a) preserved and b) impaired diastolic relaxation demonstrating reduced first-phase ejection fraction, sustained myocardial contraction in the subject with impaired diastolic relaxation. Both subjects had preserved EF (63.4% and 63.5%) and similar resting heart rate but differing first-phase ejection fraction (EF1) and time of onset of myocardial relaxation (TOR): a) E/E'=8.0, EF1=19.7%, TOR=22.0%; (b) E/E'=16.6, EF1=14.8%, TOR=61.2%.
Figure 4:
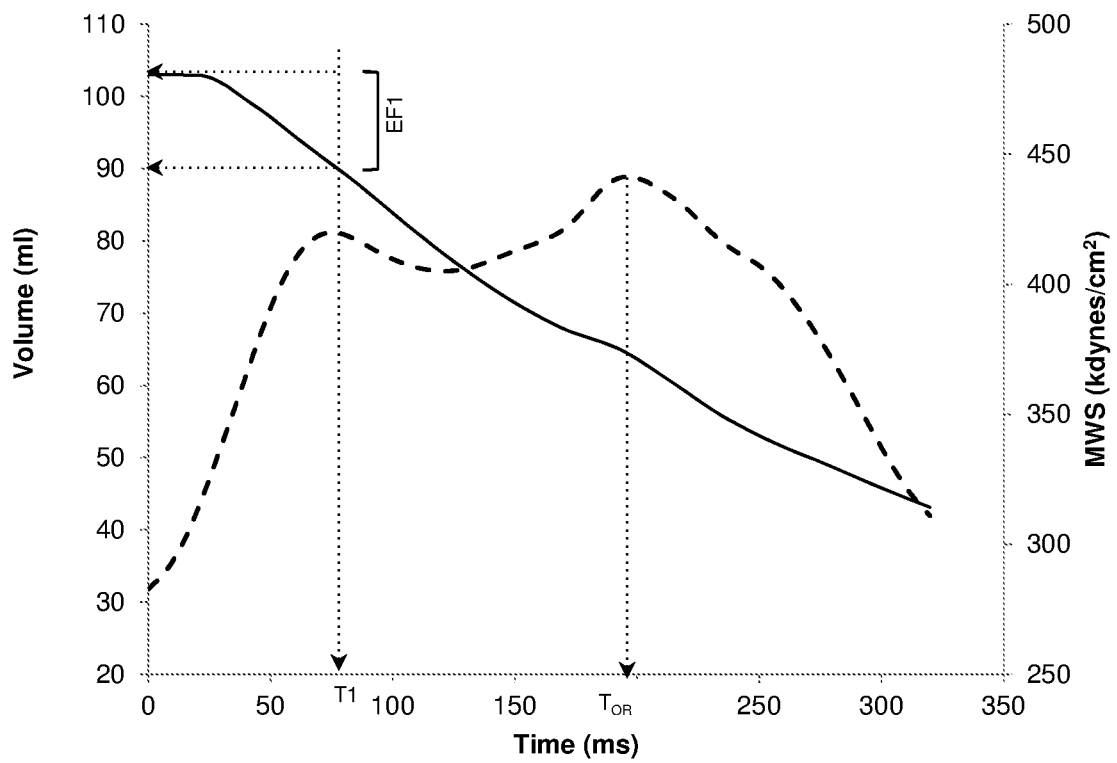

Myocardial contraction was prolonged with greater TOR in subjects with increased E/E' compared to those with lower E/E' (FIG. 3). In subjects with E/E'>9.19, TOR was 38±3% compared to 27±1% in those with E/E'<6.43 (p<0.001, irrespective of adjustment for age and gender or other covariates). On multivariate analysis TOR was positively associated with E/E' (β=0.345, p<0.0001, table 2). When examining the relation of TOR to haemodynamic events during systole, TOR was independently related only to age and EF1 (P=0.027). An example of two age and heart rate matched subjects were shown in FIG. 4.

Effect of Nitroglycerin on Systolic and Diastolic Function

Figure 5:
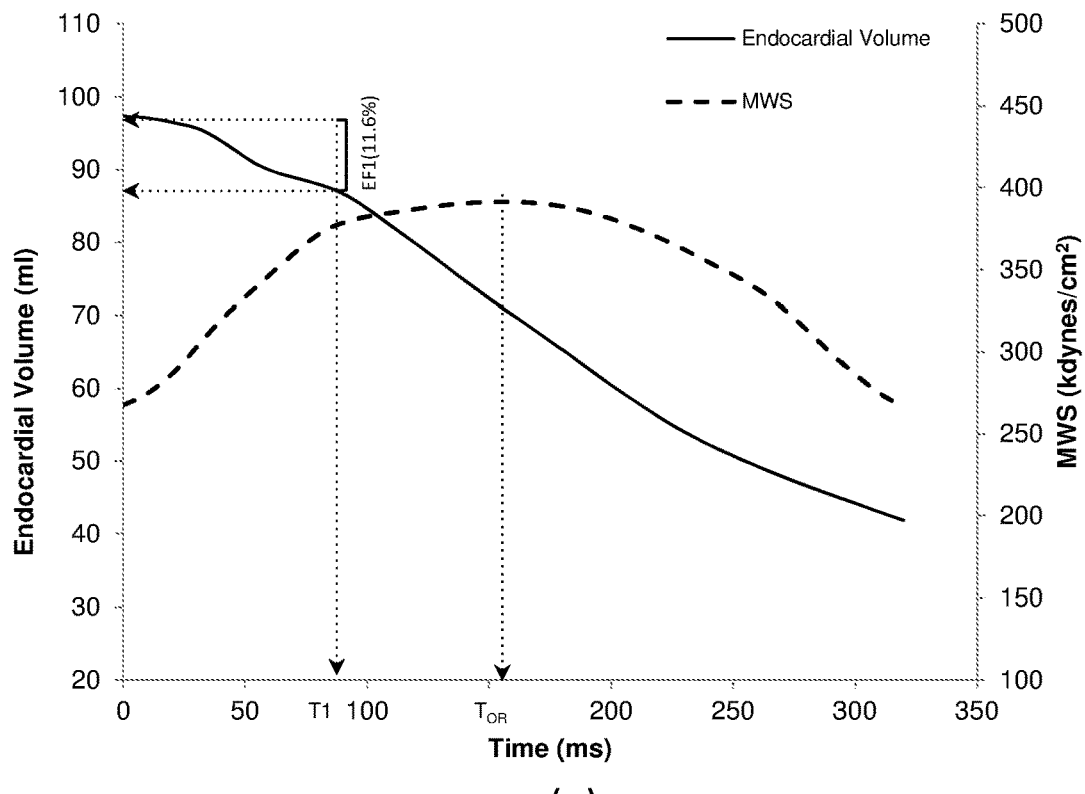
FIG. 5 shows endocardial volume and myocardial wall stress at baseline (a) and after administration of nitroglycerin (NTG) (b) in a 65 year-old male. After NTG, first-phase ejection fraction (EF1) increased from 11.6% to 17.9%, Time from end-systole to onset of relaxation (TOR) also reduced significantly from 53 to 32%.
Figure 5:
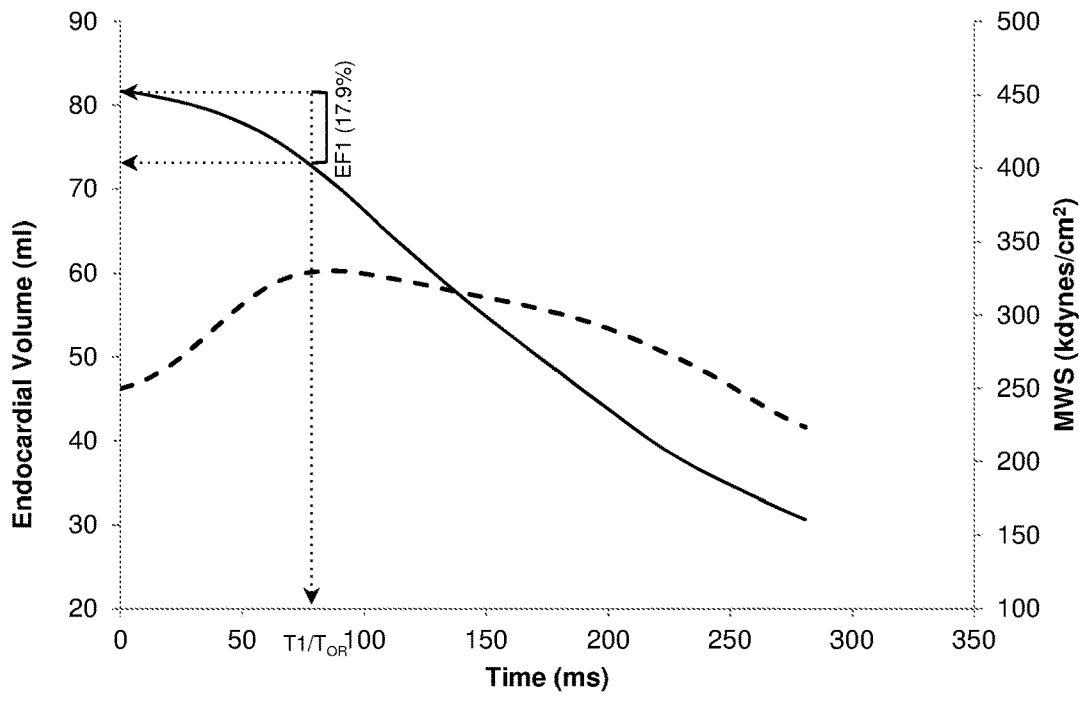

NTG produced a modest but significant reduction in blood pressure (table 3). It had no significant effect on EF but increased EF1 significantly by 5.0±1.8% from 15.2±1.8 to 20.3±2.6%, (P<0.001), reduced TOR from 41.7±3.6 to 32.5±1.7% (P<0.05) and reduced E/E' from 8.5±0.6 to 6.6±0.5 (P=0.014). FIG. 5 showed an example of one subject with increasing in EF1 and reduction of TOR.

Discussion

Shortening deactivation of myocyte contraction in vivo is likely to involve a transduction of shortening that occurs early in systole at or before T1 since, in healthy subjects, the myocardium starts to relax from this point onwards.[3] The major novelty of the present work is the introduction of first-phase ejection fraction, EF1, as a potential measure of the shortening that triggers deactivation and which, if impaired, leads to sustained contraction that may compromise diastolic relaxation. The main experimental findings are that, in hypertensive subjects with hypertension of varying severity and with varying structural remodeling, there is a striking relationship between EF1, TOR and diastolic relaxation as assessed by E/E', a robust measure of diastolic function which is one of the best predictors of outcome in hypertension.[13] EF1 and TOR are strongly related to E/E' independent of ventricular cavity and wall dimensions and of afterload as assessed by PWV and blood pressure. Furthermore, when examining events during systole, TOR is independently related to EF1. Whilst these associations were independent of ventricular geometry they could be secondary to structural changes such as interstitial fibrosis. However, our studies with NTG, demonstrate that an increase in EF1 is associated with a reduction in TOR and improved diastolic relaxation, demonstrating that diastolic relaxation can be modified and supporting a causal effect of EF1 on subsequent contraction/relaxation dynamics. To what degree changes in EF1 were due to a reduction in preload/afterload or to a direct action of NTG on the myocardium cannot be determined from the present study but previous studies have shown that intra-coronary injection of NTG and other NO donors has a direct effect on ventricular dynamics.[5,6] This, combined with lack of association of diastolic function with measures of afterload, would suggest a direct effect of NTG or one that is mediated through a reduction in pre-load.

Although diastolic dysfunction with preserved overall EF is recognized as a distinct phenotype,[14] it is also accepted that diastolic dysfunction often co-exists with systolic dysfunction, particularly systolic dysfunction that may not manifest as a reduction in overall EF.[15] The present study supports this view with an emphasis on first phase ejection fraction as a potential primary determinant of subsequent events in systole and diastole. It demonstrates that profound degrees of early systolic dysfunction resulting in a reduction in EF1 of >25% are seen in the absence of any change in overall EF. The sustained contraction that is seen in association with a reduced EF1 may represent a compensatory mechanism to maintain the overall EF, so that this is preserved even in the face of marked early systolic dysfunction. A link between early systolic and diastolic dysfunction mediated by a reverse of the shortening deactivation phenomenon would explain why E/E' is prolonged after myocardial infarction and after angioplasty and is a good predictor of outcome after events such as these[16,17] that would not necessarily be expected to impact on diastolic relaxation per se.

Our study is subject to a number of important limitations. First, our conclusions relate only to hypertensive subjects. We studied these because of the importance of hypertension as a risk factor for heart failure with preserved ejection fraction and relatively modest departure from normal physiology. Further studies will be required to establish the nature of the link between early systolic dysfunction, sustained myocardial contraction and impaired diastolic relaxation in cardiomyopathies of differing aetiologies and severity. Conclusions regarding causality cannot be drawn from the cross-sectional observations, although effects of NTG and biological plausibility support a causal role of EF1. We used non-invasive estimates of left ventricular pressure and wall stress that are limited by calibration of non-invasive blood pressure. However, whilst calibration errors might influence absolute values, they are less likely to influence the relative timing of wall stress. Our measures of ventricular volumes were obtained from a single plane across the ventricle and thus provide a two-dimensional measure of shortening. Three-dimensional imaging will be required to determine whether alternative measures perform similarly and to assess first phase ejection in subjects with regional wall abnormalities.

In conclusion, our findings provide a potential mechanistic link between early systolic dysfunction, sustained myocardial contraction and impaired diastolic relaxation. In hypertensive patients, reduced first phase ejection is associated with sustained contraction and impaired diastolic relaxation. First phase ejection fraction linked to subsequent contraction/relaxation through the shortening deactivation phenomenon may be an important diagnostic measurement and therapeutic target to prevent progression to heart failure, particularly that associated with hypertension and preserved ejection fraction.

Various modifications, whether by way of addition, deletion, or substitution may be made to the above mentioned embodiments to provide further embodiments, any and all of which are intended to be encompassed by the appended claims.

TABLE 1

Subject characteristics according to E/E'

| | E/E' < 6.44 (n = 74) | E/E': 6.44-9.18 (n = 61) | E/E' > 9.18 (n = 28) | P value |
|---|---|---|---|---|
| Characteristic | | | | |
| Age (years) | 39.5 ± 15.1 | 50.9 ± 15.2 | 55.4 ± 15.4 | 0.001 |
| Male Sex (%) | 59.5% | 42.6% | 39.3% | 0.139 |
| BMI (kg/m$^2$) | 26.7 ± 0.5 | 26.8 ± 0.6 | 28.2 ± 0.8 | 0.305 |
| Anti-hypertensives (%) | 51.0% | 55.6% | 85% | <0.001 |
| Heart rate, blood pressure and PWV | | | | |
| Heart rate (bpm) | 69 ± 12 | 67 ± 10 | 72 ± 12 | 0.127 |
| SBP (mmHg) | 131 ± 16 | 138 ± 21 | 154 ± 26 | <0.001 |
| DBP (mmHg) | 79 ± 11 | 84 ± 12 | 87 ± 18 | 0.007 |
| MAP (mmHg) | 96 ± 12 | 103 ± 16 | 112 ± 20 | <0.001 |
| cSBP (mmHg) | 117 ± 15 | 128 ± 21 | 145 ± 28 | <0.001 |
| PWV (m/s) | 4.1 ± 1.3 | 4.2 ± 1.5 | 5.3 ± 1.5 | <0.001 |

TABLE 1-continued

Subject characteristics according to E/E'

| | E/E' < 6.44 (n = 74) | E/E': 6.44-9.18 (n = 61) | E/E' > 9.18 (n = 28) | P value |
|---|---|---|---|---|
| LV Geometry | | | | |
| EDV (ml) | 114.3 ± 32.4 | 102.4 ± 29.4 | 101.1 ± 33.6 | 0.048 |
| LVMI (g/m$^2$) | 77.5 ± 22.9 | 81.6 ± 21.4 | 98.1 ± 28.7 | 0.001 |
| LV Dynamics | | | | |
| EF (%) | 58.5 ± 6.1 | 57.5 ± 6.4 | 58.5 ± 7.7 | 0.631 |
| GLS (%) | −18.2 ± 0.8 | −17.9 ± 0.9 | −14.7 ± 2.0 | 0.089 |
| E/E' | 5.24 ± 0.80 | 7.57 ± 0.71 | 11.62 ± 3.10 | <0.001 |

E/E': ratio of mitral valve Doppler early flow (E wave velocity) and tissue Doppler mitral annulus movement (E' wave velocity); BMI: body mass index; HR: heart rate; bpm: beats per minutes; SBP: systolic blood pressure; DBP: diastolic blood pressure; MAP: mean arterial pressure; cSBP: central systolic blood pressure; PWV: pulse wave velocity; LV: Left ventricle; EDV: end diastolic volume; LVMI: left ventricular mass index; EF: ejection fraction; GLS: global longitudinal strain.

TABLE 2

Multivariate Analysis of relations between EF1 and E/E' and between TOR and E/E'

| | EF1 | | TOR | |
|---|---|---|---|---|
| Covariate | β | P Value | β | P Value |
| Model 1 (Enter) | | | | |
| Age (years) | 0.071 | 0.504 | 0.039 | 0.733 |
| Gender | −0.199 | 0.033 | 0.004 | 0.968 |
| BMI (kg/m$^2$) | 0.126 | 0.110 | 0.095 | 0.258 |
| HR (bpm) | 0.012 | 0.887 | −0.097 | 0.280 |
| SBP (mmHg) | 0.076 | 0.692 | 0.282 | 0.169 |
| DBP (mmHg) | −0.260 | 0.113 | −0.186 | 0.287 |
| PWV (m/s) | 0.014 | 0.911 | −0.024 | 0.860 |
| AV Peak Flow (m/s) | 0.079 | 0.465 | −0.152 | 0.190 |
| EDV (ml) | −0.049 | 0.623 | −0.144 | 0.176 |
| LVMI (g/m$^2$) | −0.024 | 0.803 | −0.045 | 0.665 |
| T1 (ms) | 0.078 | 0.038 | 0.157 | 0.131 |
| Anti-hypertensive | 0.166 | 0.046 | −0.003 | 0.97 |
| E/E' | −0.363 | <0.001 | 0.347 | 0.001 |
| Model 2 (Stepwise) | | | | |
| Gender | −0.236 | 0.001 | — | — |
| DBP (mmHg) | −0.245 | 0.001 | — | — |
| Anti-hypertensive | 0.160 | 0.030 | — | — |
| E/E' | −0.341 | <0.001 | 0.403 | <0.001 |

EF1: 1$^{st}$ phase ejection fraction; T$_{OR}$: time to onset of relaxation; BMI: body mass index; HR: heart rate; bpm: beats per minute; SBP: systolic blood pressure; DBP: diastolic blood pressure; PWV: pulse wave velocity; AV: aortic valve; EDV: end-diastolic volume; LVMI: left ventricular mass index; T1: time to first systolic peak on pressure waveform; E/E': ratio of mitral valve Doppler early flow (E wave velocity) and tissue Doppler mitral annulus movement (E' wave velocity).

TABLE 3

Effects of nitroglyerin on blood pressure, systolic and diastolic function

| Measure | Baseline | NTG | Difference | P value |
|---|---|---|---|---|
| Heart rate and blood pressure | | | | |
| Heart rate (bpm) | 63.9 ± 2.6 | 67.4 ± 3.2 | 3.6 ± 1.3 | 0.017 |
| SBP (mmHg) | 151 ± 7 | 145 ± 6 | −6 ± 2 | 0.027 |
| DBP (mmHg) | 90 ± 4 | 82 ± 4 | −8 ± 1 | <0.001 |
| MAP (mmHg) | 112 ± 5 | 99 ± 5 | −13 ± 1 | <0.001 |
| LV dynamics | | | | |
| EF (%) | 55.6 ± 2.9 | 59.1 ± 2.2 | 3.5 ± 1.8 | 0.072 |
| EF1 (%) | 15.2 ± 1.8 | 20.3 ± 2.6 | 5.0 ± 1.8 | 0.011 |
| T1 (ms) | 97.6 ± 3.3 | 110.9 ± 6.6 | 13.3 ± 1.3 | 0.158 |
| TOR (%) | 41.7 ± 3.6 | 32.5 ± 1.7 | −8.2 ± 3.8 | 0.046 |
| E/E' | 8.5 ± 0.6 | 6.6 ± 0.5 | −1.95 ± 0.7 | 0.014 |

NTG: nitroglycerin; SBP: systolic blood pressure; DBP: diastolic blood pressure; MAP: mean arterial pressure; LV: left ventricle; EF: ejection fraction; EF1: 1$^{st}$ phase ejection fraction; T1: time to first systolic peak on pressure waveform; T$_{OR}$: time to onset of myocardial relaxation; E/E': ratio of mitral valve Doppler early flow (E wave velocity) and tissue Doppler mitral annulus movement (E' wave velocity).

REFERENCES

1. Brady A J. Time and displacement dependence of cardiac contractility: problems in defining the active state and force-velocity relations. *Fed Proc.* 1965; 24:1410-20.
2. Brutsaert D L, de Clerck N M, Goethals M A and Housmans P R. Relaxation of ventricular cardiac muscle. *J Physiol.* 1978; 283:469-80.
3. Chirinos J A, Segers P, Gupta A K, Swillens A, Rietzschel E R, De Buyzere M L, Kirkpatrick J N, Gillebert T C, Wang Y, Keane M G, Townsend R, Ferrari V A, Wiegers S E and St John S M. Time-varying myocardial stress and systolic pressure-stress relationship: role in myocardial-arterial coupling in hypertension. *Circulation.* 2009; 119: 2798-2807.
4. Williams D O, Amsterdam E A and Mason D T. Hemodynamic effects of nitroglycerin in acute myocardial infarction. *Circulation.* 1975; 51:421-427.
5. Fok H, Guilcher A, Li Y, Brett S, Shah A, Clapp B and Chowienczyk P. Augmentation pressure is influenced by ventricular contractility/relaxation dynamics: novel mechanism of reduction of pulse pressure by nitrates. *Hypertension.* 2014; 63:1050-1055.
6. Paulus W J, Vantrimpont P J and Shah A M. Acute effects of nitric oxide on left ventricular relaxation and diastolic distensibility in humans. Assessment by bicoronary sodium nitroprusside infusion. *Circulation.* 1994; 89:2070-2078.
7. Pauca A L, Wallenhaupt S L, Kon N D and Tucker W Y. Does radial artery pressure accurately reflect aortic pressure? *Chest.* 1992; 102:1193-1198.
8. Van Bortel L M, Balkestein E J, van der Heijden-Spek J J, Vanmolkot F H, Staessen J A, Kragten J A, Vredeveld J W, Safar M E, Struijker Boudier H A and Hoeks A P. Non-invasive assessment of local arterial pulse pressure: comparison of applanation tonometry and echo-tracking. *Journal of hypertension.* 2001; 19:1037-44.
9. Chen C H, Ting C T, Nussbacher A, Nevo E, Kass D A, Pak P, Wang S P, Chang M S and Yin F C. Validation of carotid artery tonometry as a means of estimating augmentation index of ascending aortic pressure. *Hypertension.* 1996; 27:168-175.
10. Davies J E, Whinnett Z I, Francis D P, Willson K, Foale R A, Malik I S, Hughes A D, Parker K H and Mayet J. Use of simultaneous pressure and velocity measurements to estimate arterial wave speed at a single site in humans. *American journal of physiology Heart and circulatory physiology.* 2006; 290:H878-85.
11. Lang R M, Bierig M, Devereux R B, Flachskampf F A, Foster E, Pellikka P A, Picard M H, Roman M J, Seward J, Shanewise J S, Solomon S D, Spencer K T, Sutton M S, Stewart W J, Chamber Quantification Writing G, American Society of Echocardiography's G, Standards C and European Association of E. Recommendations for chamber quantification: a report from the American Society of Echocardiography's Guidelines and Standards Committee and the Chamber Quantification Writing Group, developed in conjunction with the European Association of Echocardiography, a branch of the European Society of Cardiology. *Journal of the American Society of Echocardiography: official publication of the American Society of Echocardiography.* 2005; 18:1440-63.
12. Arts T, Bovendeerd P H, Prinzen F W and Reneman R S. Relation between left ventricular cavity pressure and volume and systolic fiber stress and strain in the wall. *Biophysical journal.* 1991; 59:93-102.
13. Sharp A S, Tapp R J, Thom S A, Francis D P, Hughes A D, Stanton A V, Zambanini A, O'Brien E, Chaturvedi N, Lyons S, Byrd S, Poulter N R, Sever P S, Mayet J and Investigators A. Tissue Doppler E/E' ratio is a powerful predictor of primary cardiac events in a hypertensive population: an ASCOT substudy. *European heart journal.* 2010; 31:747-52.
14. McMurray J J, Adamopoulos S, Anker S D, Auricchio A, Bohm M, Dickstein K, Falk V, Filippatos G, Fonseca C, Gomez-Sanchez M A, Jaarsma T, Kober L, Lip G Y, Maggioni A P, Parkhomenko A, Pieske B M, Popescu B A, Ronnevik P K, Rutten F H, Schwitter J, Seferovic P, Stepinska J, Trindade P T, Voors A A, Zannad F, Zeiher A and Guidelines ESCCf P. ESC Guidelines for the diagnosis and treatment of acute and chronic heart failure 2012: The Task Force for the Diagnosis and Treatment of Acute and Chronic Heart Failure 2012 of the European Society of Cardiology. Developed in collaboration with the Heart Failure Association (HFA) of the ESC. *Eur Heart J.* 2012; 33:1787-847.
15. Petrie M C, Caruana L, Berry C and McMurray J J. "Diastolic heart failure" or heart failure caused by subtle left ventricular systolic dysfunction? *Heart.* 2002; 87:29-31.
16. Hillis G S, Moller J E, Pellikka P A, Gersh B J, Wright R S, Ommen S R, Reeder G S and Oh J K. Noninvasive estimation of left ventricular filling pressure by E/e' is a powerful predictor of survival after acute myocardial infarction. *J Am Coll Cardiol.* 2004; 43:360-7.
17. Naqvi T Z, Padmanabhan S, Rafii F, Hyuhn H K and Mirocha J. Comparison of usefulness of left ventricular diastolic versus systolic function as a predictor of outcome following primary percutaneous coronary angioplasty for acute myocardial infarction. *Am J Cardiol.* 2006; 97:160-6.

The invention claimed is:

1. A computer-implemented method, comprising:
i) monitoring, using a left ventricle monitoring device, a left ventricle volume of a test subject during at least a first part of a cardiac cycle;
ii) determining, by a data processing device in communication with the left ventricle monitoring device, a point in time (T1) in the cardiac cycle which is the end of a first phase of ventricular contraction during the first part of the cardiac cycle;
iii) making a first measurement of the left ventricle volume at a start of the first part of the cardiac cycle and a second measurement of the left ventricle volume at the determined point in time in the cardiac cycle which is the end of the first phase of ventricular contraction; and
iv) calculating, by the data processing device, a first phase ejection measurement in dependence on the first measurement of the left ventricle volume made at the start of the first part of the cardiac cycle and the second measurement of the left ventricle volume made at the determined point in time in the cardiac cycle which is the end of the first phase of ventricular contraction; and
v) outputting on a display, by the data processing device, the calculated first phase ejection measurement to allow diagnosing of diastolic dysfunction of the test subject in the event that the calculated first phase ejection measurement is reduced when compared to that expected from a healthy test subject,
wherein the point in time in the cardiac cycle which is the end of the first phase of ventricular contraction is the point in time that corresponds to peak aortic flow or peak aortic flow velocity; and
wherein the first part of the cardiac cycle is the systolic phase of the cardiac cycle and the data processing device determines the first phase ejection measurement in dependence on the difference in left ventricle volume at the start of the systolic phase of the cardiac cycle and at the determined point in time, and the first phase ejection measurement is a first phase ejection fraction (EF1) calculated using:

$$EF1=(EDV-T1V)/EDV$$

where EDV is an end-diastolic left ventricle volume, and T1V is the left ventricle volume at the determined point in time (T1).

2. A computer-implemented method according to claim 1, and further comprising:
simultaneously with the monitoring of the left ventricle volume of the test subject, monitoring systolic pressure of the test subject during at least the first part of the cardiac cycle to obtain systolic pressure waveform data; and
determining the point in time (T1) in the cardiac cycle which is the end of the first phase of ventricular contraction during the first part of the cardiac cycle in dependence on the systolic pressure waveform data.

3. A computer-implemented method according to claim 2, wherein the monitoring of the systolic pressure is undertaken using carotid tonometry techniques.

4. A computer-implemented method according claim 2, wherein the monitoring of the systolic pressure is undertaken using echocardiogram Doppler techniques.

5. A computer-implemented method according to claim 2, wherein the determining comprises differentiating the pressure waveform with respect to time, and identifying the end of the first phase of ventricular contraction from the differentiated waveform.

6. A computer-implemented method according to claim 1, wherein determining the point in time in the cardiac cycle which is the end of the first phase of ventricular contraction comprises determining an average time of a plurality of individual point-in-time measurements for the test subject.

7. A computer-implemented method according to claim 1, wherein the monitoring of the left ventricle volume is undertaken using echocardiogram speckle tracking techniques.

8. A computer-implemented method according to claim 1, wherein the monitoring of the left ventricle volume is undertaken using cardiac magnetic resonance imaging techniques.

9. A computer-implemented method according to claim 1, wherein the monitoring of the left ventricle volume comprises:
i) measuring aortic flow velocity during at least the first part of the cardiac cycle, and ii) integrating the measured aortic flow velocity with respect to time to determine the left ventricle volume at the determined point in time.

10. A computer-implemented method according to claim 1, wherein the determined point in time corresponds to peak motion in myocardial tissue and is found using tissue Doppler imaging.

11. A method according to claim 1, wherein the point in time that corresponds to peak aortic flow or peak aortic flow velocity is determined as the point in time at which any one or more of the following occurs:
   i) the rate of change of the systolic pressure during the first part of the cardiac cycle reduces;
   ii) the time of a first peak in systolic pressure;
   iii) the time of maximal rate of ventricular shortening;
   iv) the time of a first shoulder on the systolic pressure waveform; and/or
   v) the time of peak motion of myocardial tissue.

12. A system comprising:
   a left ventricle monitoring device configured to monitor a left ventricle volume of a test subject during at least a first part of a cardiac cycle of the test subject;
   a display;
   a processor in communication with the left ventricle monitoring device; and
   memory storing computer readable instructions that, when executed, configure the processor to cause the system to perform:
   i) receiving, from the left ventricle monitoring device, the left ventricle volume of the test subject during at least the first part of the cardiac cycle;
   ii) determining a point in time (T1) in the cardiac cycle which is the end of a first phase of ventricular contraction during the first part of the cardiac cycle;
   iii) making a first measurement of the left ventricle volume at a start of the first part of the cardiac cycle and a second measurement of the left ventricle volume at the determined point in time in the cardiac cycle which is the end of the first phase of ventricular contraction;
   iv) calculating a first phase ejection measurement in dependence on the first measurement of the left ventricle volume made at the start of the first part of the cardiac cycle and the second measurement of the left ventricle volume made at the determined point in time in the cardiac cycle which is the end of the first phase of ventricular contraction; and
   v) outputting on the display the first phase ejection measurement to allow diagnosing of early onset heart failure of the test subject in the event that the calculated first phase ejection measurement is reduced when compared to that expected from a healthy test subject,
   wherein the point in time in the cardiac cycle which is the end of the first phase of ventricular contraction is the point in time that corresponds to peak aortic flow or peak aortic flow velocity; and
   wherein the first part of the cardiac cycle is the systolic phase of the cardiac cycle and the first phase ejection measurement is determined in dependence on the difference in left ventricle volume at the start of the systolic phase of the cardiac cycle and at the determined point in time, and the first phase ejection measurement is a first phase ejection fraction (EF1) calculated using:

$$EF1=(EDV-T1V)/EDV$$

where EDV is an end-diastolic left ventricle volume, and T1V is the left ventricle volume at the determined point in time (T1).

13. A system according to claim 12, wherein the point in time that corresponds to peak aortic flow or peak aortic flow velocity is determined as the point in time at which any one or more of the following occurs:
   i) the rate of change of the systolic pressure during the first part of the cardiac cycle reduces;
   ii) the time of a first peak in systolic pressure;
   iii) the time of maximal rate of ventricular shortening;
   iv) the time of a first shoulder on the systolic pressure waveform; and/or
   v) the time of peak motion of myocardial tissue.

14. The system of claim 12, wherein the left ventricle monitoring device is an echo system for performing echocardiography.

15. The system of claim 12, wherein the left ventricle monitoring device is a cardiac magnetic resonance image (cMRI) scanner.

* * * * *